(12) United States Patent
Gao et al.

(10) Patent No.: US 6,514,492 B1
(45) Date of Patent: Feb. 4, 2003

(54) TASTE MASKING OF ORAL QUINOLONE LIQUID PREPARATIONS USING ION EXCHANGE RESINS

(75) Inventors: Rong Gao, Edison, NJ (US); Zezhi Jesse Shao, Basking Ridge, NJ (US); Allan Chor-Lun Fan, Berkeley Heights, NJ (US); Leonore Catherine Witchey-Lakshmanan, Piscataway, NJ (US); Daniel Charles Stewart, Cherry Hill, NJ (US)

(73) Assignee: Schering-Plough Veterinary Corporation, Reno, NV (US)

( * ) Notice: Subject to any disclaimer, the term of this patent is extended or adjusted under 35 U.S.C. 154(b) by 0 days.

(21) Appl. No.: 09/614,523

(22) Filed: Jul. 12, 2000

Related U.S. Application Data
(60) Provisional application No. 60/143,819, filed on Jul. 14, 1999.

(51) Int. Cl.⁷ ................ A61K 31/74; A61K 31/785; A61K 9/20; A61K 9/48; A61K 9/28
(52) U.S. Cl. ............ 424/78.1; 424/78.12; 424/78.14; 424/400; 424/464; 424/451; 424/474; 424/486
(58) Field of Search ............... 424/78.12, 78.1, 424/400, 78.14, 464, 451, 474, 486

(56) References Cited

U.S. PATENT DOCUMENTS

| | | | |
|---|---|---|---|
| 2,990,332 A | 6/1961 | Keating | 167/65 |
| 4,808,411 A | 2/1989 | Lu et al. | 424/441 |
| 5,032,393 A | 7/1991 | Douglas et al. | 424/79 |
| 5,084,276 A | 1/1992 | Yunker et al. | 424/422 |
| 5,152,986 A * | 10/1992 | Lange et al. | 424/78.14 |
| 5,219,563 A | 6/1993 | Douglas et al. | 424/78.1 |
| 5,275,820 A | 1/1994 | Chang | 424/426 |
| 5,286,489 A * | 2/1994 | Tsau | 424/440 |
| 5,730,997 A | 3/1998 | Lienhop et al. | 424/439 |

FOREIGN PATENT DOCUMENTS

| | | | |
|---|---|---|---|
| EP | 0 225 615 A2 | 6/1987 | A61K/9/22 |
| EP | 0 622 083 A1 | 11/1994 | A61K/47/48 |
| GB | 934285 | 8/1963 | |
| GB | 942873 | 11/1963 | |
| WO | WO 93/05816 | 4/1994 | A61K/47/48 |

OTHER PUBLICATIONS

Borodkin et al., "Polycarboxylic Acid Ion–Exchange Resin Adsorbates for Taste Coverage in Chewable Tablets," *Journal of Pharmaceutical Sciences*, vol. 60, No. 10 (1971).

* cited by examiner

Primary Examiner—Thurman K. Page
Assistant Examiner—Blessing Fubara

(57) ABSTRACT

This invention relates to the formulation of oral liquid products of quinolones or derivatives thereof using ion exchange resins, such as methacrylic acid polymer crosslinked with divinylbenzene, as the carrier, thereby eliminating the extreme bitterness of the quinolones oral liquid formulation.

6 Claims, No Drawings

TASTE MASKING OF ORAL QUINOLONE LIQUID PREPARATIONS USING ION EXCHANGE RESINS

CROSS-REFERENCE TO RELATED APPLICATIONS

This application claims priority, pursuant to 35 USC §119(e), to provisional application No. 60/143,819, filed Jul. 14, 1999, the entire disclosure of which is incorporated herein for all purposes.

BACKGROUND OF THE INVENTION

1. Field of the Invention

The present invention relates to the formulation of oral liquid preparations of quinolones or derivatives thereof using ion exchange resins, such as a methacrylic acid polymer crosslinked with divinylbenzene, as the carrier. The formation of a quinolone-resin complex (resinate) eliminates the extreme bitterness of the quinolones to make the liquid oral dosage form palatable.

2. Description of Related Art

Quinolone antibiotics are widely used in the treatment of common infections. The current quinolone products on the market, including orbifloxacin, and ciprofloxacin, are administered as tablets or capsules. Since quinolones have an extremely bitter taste, development of palatable liquid oral dosage forms has always been challenging. Liquid oral dosage forms are useful for patients having difficulty swallowing capsules or tablets. The Journal of Pharm. Sciences, vol 60, No 10, pp 1523–1527 (October 1971) discloses polycarboxylic acid ion exchange resins as adsorbates for masking the bad taste of ephedrine, dextromethorphan, pseudoephedrine, and methapyrilene; EPO 225615, published Jun. 16, 1987, discloses liquid pharmaceutical compositions containing dextrometorphan, ion exchange resin (preferably a cationic resin) and acceptable pharmaceutical carriers, sweetners and formulation aids. Taste is not an issue. U.S. Pat. No. 4,808,411 issued Feb. 28, 1989 discloses antibiotic polymer compositions containing acrylic acid polymers and erythromycin. Said compositions can be prepared as liquids and are effective in masking the taste of the erythromycin antibiotic; U.S. Pat. No. 5,152,986, issued Oct. 6, 1992, discloses pharmaceutical compositions containing quinolone carboxylic acid derivatives (such as ciprofloxacin) and ion exchange resins (preferably cationic) which mask the bad taste of the quinolone in animal feeds. Said compositions are in solid form and paste form; EPO 622083, published Nov. 11, 1994, discloses a solid pharmaceutical preparation containing any number of therapeutic agents, such as β-lactam antibiotics, antihistamines, bronchodilators and antiinflammatories, and cationic or anionic ion exchange resins which decrease the unpleasant taste and odor of the therapeutic agent.

There is still a need in the art for oral liquid quinolone preparations with acceptable taste. Applicants have satisfied this need in the art by preparing liquid quinolone preparations with acceptable taste.

DEFINITIONS AND USAGES OF TERMS

The term "pharmaceutical composition", as used herein, means a combination comprised of a safe and effective amount of the quinolone compound active ingredient, or mixtures thereof, and pharmaceutically-acceptable excipients.

The term "pharmaceutically acceptable excipients", as used herein, means any physiologically inert, pharmacologically inactive material known to one skilled in the art, which is compatible with the physical and chemical characteristics of the particular quinolone compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "ion exchange resin", as used herein, means anionic or cationic ion exchange resins.

The term "oral dosage form", as used herein, means any pharmaceutical composition intended to be systemically administered to an individual by delivering said composition to the gastrointestinal tract of an individual, via the mouth of said individual. Oral dosage forms include, tablets, coated or non-coated; liquids, such as solutions and suspensions; or capsules, coated or non-coated.

All percentages are on a weight percent basis unless otherwise indicated.

BRIEF SUMMARY OF THE INVENTION

The present invention relates to an aqueous pharmaceutical composition comprising:
 a. 0.01% to 30% by weight of a quinolone compound or derivative thereof;
 b. 0.01% to 60% by weight of an ion exchange resin;
 c. pharmaceutically acceptable excipients to equal 100%.

DETAILED DESCRIPTION OF THE INVENTION

The present invention relates to an aqueous pharmaceutical composition comprising:
 a. 0.01% to 30% by weight of a quinolone compound or derivative thereof;
 b. 0.01% to 60% by weight of an ion exchange resin;
 c. pharmaceutically acceptable excipients to equal 100%.

Quinolones and Derivatives Thereof Useful in the Practice of the Present Invention Quinolones and derivatives thereof useful in the practice of the present invention include, but are not limited to, orbifloxacin, ciprofloxacin, danofloxacin, enoxacin, grepafloxacin, levofloxacin,lomefloxacin, nalidixic acid, norfloxacin, ofloxacin,sparfloxacin, and trovafloxacin mesylate. The preferred quinolone is orbifloxacin available from Schering Plough, Kenilworth, N.J. as ORBAX®. Other quinolones useful in the practice of the present invention are described in WO 96/16055 published May 30, 1996; U.S. Pat. No. 5,104,868 issued Apr. 14, 1992; U.S. Pat. No. 5,496,947 issued Mar. 5, 1996; U.S. Pat. No. 5,498,615 issued Mar. 12, 1996; U.S. Pat. No. 5,770,597 issued Jun. 23, 1998; U.S. Pat. No. 5,840,333 issued Nov. 24, 1998; U.S. Pat. No. 5,672,600 issued Sep. 30, 1997; U.S. Pat. No. 5,491,139 issued Feb. 13, 1996; U.S. Pat. No. 5,530,116 issued Jun. 25, 1996; and U.S. Pat. No. 5,646,163 issued Jul. 8, 1997, all incorporated by reference herein.

The quinolone compounds useful in the practice of the present invention comprise from about 0.01% to about 30% by weight of the pharmaceutical compositions of the present invention. Preferably, the quinolone compounds useful in the practice of the present invention comprise from about 0.1% to about 10% by weight of the pharmaceutical compositions of the present invention. More preferably, the quinolone compounds useful in the practice of the present invention comprise from about 0.5% to 5% by weight of the pharmaceutical compositions of the present invention.

Ion Exchange Resins Useful in the Practice of the Present Invention Ion exchange resins useful in the practice of the present invention include, but are not limited to, anionic resins such as: DUOLITE® AP143/1083 (cholestyramine resin USP) and cationic resins such as: AMBERLITE® IRP-64 (a porous copolymers of methacrylic acid crosslinked with divinylbenzene), AMBERLITE® IRP-69 (Sodium polystyrene sulfonate USP) and AMBERLITE® IRP-88 (Polacrilin Potassium). AMBERLITE® IRP 64 is preferred resin. The DUOLITE® and AMBERLITE® resins are available from the Rohm and Haas Company, Philadelphia, Pa. The DOWEX® resins, available from the Dow Chemical Company, Midland, Mich. are also useful in the practice of the present invention. Said DOWEX® resins are strong cationic exchangers based upon polystyrenesulphonic acid with variable crosslinking (1–12% divinylbenzene) in a variety of particle sizes.

Further, said AMBERLITE® IRP 69 (sodium polystyrenesulfonate) is available commercially as a sodium salt. However, it is within the scope of the present invention to convert the sodium salt to other salt forms including, but not limited to, K and Li.

The ion exchange resins useful in the practice of the present invention comprise from about 0.01% to about 60% by weight of the pharmaceutical compositions of the present invention. Preferably the ion exchange resins useful in the practice of the present invention comprise from about 0.2% to about 20% by weight of the pharmaceutical compositions of the present invention. More preferably, the ion exchange resins useful in the practice of the present invention comprise from about 0.5% to 15% by weight of the pharmaceutical compositions of the present invention Pharmaceutically Acceptable Excipients Useful in the Practice of the Present Invention As stated hereinabove, pharmaceutically-acceptable excipients include, but are not limited to, resins, fillers, binders, lubricants, solvents, glidants, disintegrants, co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences,* 18th Edition, Mack Publishing Company, 1990, pp. 1288–1300, incorporated by reference herein. The pharmaceutical compositions suitable for use herein generally contain from 0–5% flavoring agents. Preferred co-solvents include, but are not limited to, ethanol, glycerin, propylene glycol, polyethylene glycols. The pharmaceutical compositions of the present invention include from 0.01% to 30% co-solvents.

Preferred buffer systems include, but are not limited to, NaOH, acetic, boric, carbonic, phosphoric, succinic, malaic, tartaric, citric, benzoic, lactic, glyceric, gluconic, glutaric and glutamic acids and their sodium, potassium and ammonium salts. The pharmaceutical composition of the present invention generally contain from 0.1% to 20% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids.

Preferred preservatives include, but are not limited to, phenol, alkyl esters of parahydroxybenzoic acid, sorbic acid, and methylparaben, o-phenylphenol benzoic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred is sorbic acid. The compositions of the present invention generally include from 0.01% to 5% preservatives.

Preferred sweeteners include, but are not limited to, sucrose, glucose, saccharin, sorbitol, malt extract syrup, mannitol, and aspartame. Particularly preferred is malt extract syrup. Sweeteners such as sucrose, glucose, saccharin and sorbitol are generally used at levels of 0.1% to 10%. Sweeteners such as malt extract syrup are generally used at levels of 10% to 75%.

Preferred viscosity agents include, but are not limited to, methylcellulose, sodium carboxymethylcellulose, hydroxypropyl-methylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0.1% to 5% viscosity agents.

The compositions of the present invention may optionally contain lactose, mannitol, sorbitol, tribasic calcium phosphate, dibasic calcium phosphate, compressible sugar, starch, calcium sulfate, dextro and microcrystalline cellulose, magnesium stearate, stearic acid, talc, colloidal silicon dioxide, starch, sodium starch glycolate, crospovidone, croscarmelose sodium, and microcrystalline cellulose, acacia, tragacanth, hydroxypropylcellulose, pregelantinized starch, gelatin, povidone, ethylcellulose, hydroxypropylcellulose, hydroxypropylmethylcellulose, and methylcellulose.

Preparing the Compositions of the Present Invention

The compositions of the present invention are prepared according to methods known to those skilled in the art. Basically, the preparation procedure involves dissolving the quinolone in an aqueous media followed by the addition of an ion exchange resin to form a drug/resin complex. The complex can be suspended directly into suitable vehicles with flavor agents such as, but not limited to, a syrup base (malt extract) with the aid of an anticaking agent such as, but not limited to, colloidal silicone dioxide and a preservative, such as, but not limited to, sorbic acid.

The drug/resin complex can also be isolated and dried for later usage. This would be advantageous when reconstitution in the pharmacy is desired or very bitter drugs are being employed. Specifically, the quinolone and ion exchange resin complex can be blended with, for example, lactose, magnesium stearate, silicon dioxide, talc, microcrystalline cellulose or gelatin, to prepare a powder that can be shipped to the pharmacy and reconstituted into a palatable oral liquid dosage form by the pharmacist. For very bitter drugs, the drug/resin complex can be isolated, for example, by rinsing with deionized water, from uncomplexed (or free) drug. The isolated and dried powder will contain substantially only drug/resin complex. This isolated, purer drug/resin complex (substantially devoid of free drug) can be formulated into an oral liquid preparation that contains little to no amount of the bitter free drug.

The following nonlimiting Examples 1 & 2 illustrate the compositions of the present invention. Said Examples are prepared on a weight to volume (w/v) basis.

EXAMPLE 1

Purified water, USP pure—33.75%
Orbifloxacin—2%
Lactic Acid, USP to pH 4.5

Sodium Polystyrene Sulfonate ion exchange resin (USP)—12%
Malt Extract—65%
Propylene Glycol—2.5%
Sorbic Acid—0.1%
Purified water, USP Pure to equal 100%

The general procedure for preparing the composition described in Example 1 is as follows:

1) Charge orbifloxacin into water and mix well.
2) Add Lactic acid and adjust pH to 4.5
3) Charge sodium polystyrene sulfonate resin and mix well to form a slurry.
4) Charge malt extract syrup to slurry and mix well.
5) Dissolve sorbic acid in propylene glycol and charge it into slurry formed in steps 3 and 4.
6) Add water to equal 100%, weight to volume.

EXAMPLE 2

Purified Water, USP—45%
Orbifloxacin—3%
Lactic Acid to pH, 4.5
AMBERLITE IRP-64—15%
50% w/w NaOH to pH 5.5
Sorbic Acid—0.1%
Propylene Glycol—10%
Colloidal Silicon Dioxide—1.5%
Malt Extract to equal 100%

The general procedure for preparing the composition described in Example 2 is as follows:

1) Charge orbifloxacin into water and mix well.
2) Add Lactic acid to adjust pH to 4.5
3) Charge Amberlite® IRP-64 and mix well to form a slurry.
4) Adjust pH to 5.5 by adding 50% w/w NaOH.
5) Dissolve sorbic acid in propylene glycol and add it to the pH adjusted slurry.
6) Add colloidal silicon dioxide and mix well.
7) Add malt extract syrup to equal 100%, weight to volume.

What is claimed is:

1. An aqueous pharmaceutical composition comprising:
   (a) 0.01% to 30% by weight of orbifloxacin;
   (b) 0.01% to 60% by weight of an ion exchange resin; and
   (c) the remainder of the composition comprising one or more pharmaceutically acceptable excipients;
   wherein the orbifloxacin has a bitter taste that is eliminated or reduced by the ion exchange resin.

2. The composition according to claim 1, wherein the ion exchange resin is cationic.

3. The composition according to claim 2, wherein the ion exchange resin is a methacrylic acid polymer crosslinked with divinylbenzene.

4. The composition according to claim 3, wherein the ion exchange resin comprises from about 0.5% to 15% by weight of the composition.

5. The composition according to claim 1, wherein the orbifloxacin comprises from about 0.5% to 5% by weight of the composition.

6. An aqueous pharmaceutical composition comprising:
   (a) 0.01% to 30% by weight of grepafloxacin, nalidixic acid, sparfloxacin or trovafloxacin mesylate;
   (b) 0.01% to 60% by weight of an ion exchange resin; and
   (c) the remainder of the composition comprising one or more pharmaceutically acceptable excipients;
   wherein the grepafloxacin, nalidixic acid, sparfloxacin or trovafloxacin mesylate has a bitter taste that is eliminated or reduced by the ion exchange resin.

* * * * *